United States Patent
Pullagurla et al.

(10) Patent No.: US 11,180,533 B2
(45) Date of Patent: Nov. 23, 2021

(54) PROCESS FOR THE PREPARATION OF CETRORELIX ACETATE

(71) Applicant: BIOPHORE INDIA PHARMACEUTICALS PRIVATE LIMITED, Hyderabad (IN)

(72) Inventors: Manik Reddy Pullagurla, Hyderabad (IN); Jagadeesh Babu Rangisetty, Hyderabad (IN)

(73) Assignee: BIOPHORE INDIA PHARMACEUTICALS PRIVATE LIMITED, Hyderabad (IN)

( * ) Notice: Subject to any disclaimer, the term of this patent is extended or adjusted under 35 U.S.C. 154(b) by 0 days.

(21) Appl. No.: 16/441,238

(22) Filed: Jun. 14, 2019

(65) Prior Publication Data

US 2019/0382447 A1 Dec. 19, 2019

(30) Foreign Application Priority Data

Jun. 16, 2018 (IN) .............................. 201841022595

(51) Int. Cl.
  *C07K 7/23* (2006.01)
  *C07K 1/16* (2006.01)
  *C07K 1/06* (2006.01)

(52) U.S. Cl.
  CPC ............... *C07K 7/23* (2013.01); *C07K 1/063* (2013.01); *C07K 1/065* (2013.01); *C07K 1/16* (2013.01)

(58) Field of Classification Search
  CPC .......... C07K 1/063; C07K 1/065; C07K 1/16; C07K 7/23
  See application file for complete search history.

(56) References Cited

U.S. PATENT DOCUMENTS 6,258,933 B1  7/2001  Günther et al.

FOREIGN PATENT DOCUMENTS

| CN | 101284863 | * | 10/2008 | ............... C07K 1/04 |
| CN | 104610433 | * | 5/2013 | ............... C07K 7/23 |
| CN | 104861042 | * | 5/2015 | ............... C07K 7/23 |
| CN | 104892732 | * | 6/2015 | ............... C07K 7/23 |

OTHER PUBLICATIONS

Roge et al., "Brief Review on: Flash Chromatography", IJPSR, 2011, vol. 2, No. 8, pp. 1930-1937. (Year: 2011).*
CN104861042 English machine translation from patents.google.com., 8 pages, (Year: 2015).*
INDION 810, Ion Exchange—Refreshing the Planet. accessed online at https://ionresins.com/pdf/pds/810_PDS.pdf on Dec. 3, 2020, 2 pages. (Year: 2020).*

* cited by examiner

*Primary Examiner* — Marcela M Cordero Garcia
(74) *Attorney, Agent, or Firm* — McCormick, Paulding & Huber PLLC

(57) ABSTRACT

The present invention relates to an improved process for the preparation of Cetrorelix acetate (1). More particularly, the present invention relates to the purification of Cetrorelix acetate (1) by simple method.

(1)

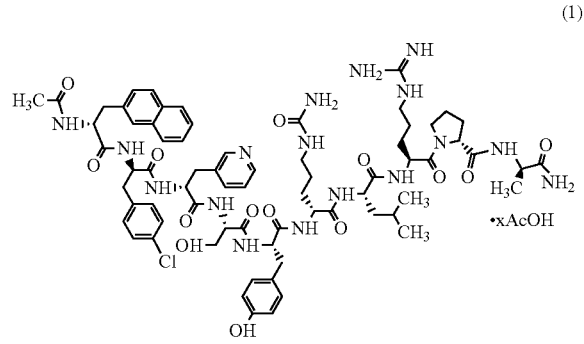

Cetrorelix acetate

10 Claims, No Drawings

PROCESS FOR THE PREPARATION OF CETRORELIX ACETATE

CROSS-REFERENCE TO RELATED APPLICATION

This application claims foreign priority benefits under U.S.C. § 119 to Indian Patent Application No. 201841022595 filed on Jun. 16, 2018, the content of which is hereby incorporated by reference in its entirety.

TECHNICAL FIELD

The present invention relates to a method for preparing a peptide Cetrorelix acetate (1) also known as Acetyl-D-3-(2"-naphtyl)-alanine-D-4-chlorophenylalanine-D-3-(3"-pyridyl)alanine-L-serine-L-tyrosine-D-citruline-L-leucine-L-arginine-L-proline-D-alanine-amide acetate salt by solid phase synthesis. It further discloses process for the purification of Cetrorelix acetate (1) with purity more than 99.0% by flash column chromatography.

BACKGROUND

Cetrorelix is a synthetic decapeptide with gonadotropin-releasing hormone (GnRH) antagonistic activity. Cetrorelix acetate is an analog of Cetrorelix which is chemically Acetyl-D-3-(2"-naphtyl)-alanine-D-4-chlorophenylalanine-D-3-(3"-pyridyl) alanine-L-serine-L-tyrosine-D-citruline-L-leucine-L-arginine-L-proline-D-alanine-amide. It is marketed as Cetrotide which a sterile powder for injection is and used for the inhibition of premature luteinizing hormone (LH) surges in women undergoing controlled ovarian stimulation.

Synthesis of Cetrorelix acetate was reported in few patents and non-patent literature, the contents of which are hereby incorporated as reference in their entirety.

U.S. Pat. No. 6,258,933 discloses the process for the re-salting and purification of Cetrorelix from the hydrochloride salt, dissolved in a suitable solvent, with acetic acid-containing solvents by liquid chromatography.

International Journal of Peptide Protein Research, 30, (1987) 1 discloses a method for converting peptide trifluoroacetate salts to the corresponding acetate salts, specifically isolation and purification of Growth Hormone-Release Factor, GRF (1-44)-$NH_2$ trifluoroacetate to the acetate with more than 95% yield by HPLC (High-performance liquid chromatography)

Although, traditional peptide isolation methods are available, still there is a need for improved process for preparation and purification of peptides resulting in less ambiguity and enhancing the yield and purity of the desired peptide. Hence, the present inventors, hereby report an improved process for preparation and purification of a pharmaceutically important decapeptide Cetrorelix.

SUMMARY

In one objective of the present invention is to provide an improved process for the preparation of Cetrorelix acetate (1).

Another objective of the invention is to provide process for the purification of Cetrorelix or its pharmaceutically acceptable salt especially acetate salt with greater than 99.0% purity by flash chromatography.

Yet, another objective of the present invention is to provide a process for the isolation of pure Cetrorelix as acetate salt (1) using simple desalting and salt exchange method, which is simple, economic and results in good yield, hence has industrial applicability.

Accordingly, the present invention provides an improved process for the preparation of pure Cetrorelix acetate (1).

In another embodiment, the present invention provides an improved process for preparation of Cetrorelix (2), comprising of the following steps:

a) loading first protected amino acid Fmoc-D-Alanine (13) on a suitable acid sensitive resin to obtain intermediate (12) using manual solid phase synthesizer.

b) deprotecting the Fmoc protecting group of intermediate (12) and coupling intermediate (12) with the required amino acids using a suitable coupling agent in the said order, wherein the order of amino acids are Fmoc-D-alanine, Fmoc-L-proline, Fmoc-D-Arginine(Pbf), Fmoc-L-leucine, Fmoc-D-citruline, Fmoc-O-tert-butyl-L-tyrosine, Fmoc-O-tert-butyl-L-serine, D-3-(3"-pyridyl)-D-alanine, Fmoc-D-4-chlorophenyl alanine, N-acetyl-D-3-(2-naphthyl)alanine to form protected peptide intermediate (3)

c) cleaving protected peptide intermediate (3) from the resin and deprotecting the side chain protecting groups to yield Cetrorelix trifluoroacetate (2)

d) purifying Cetrorelix trifluoro acetate (2) by Flash chromatography to obtain pure Cetrorelix trifluoro acetate (2)

e) isolating Cetrorelix acetate (1) by salt exchange method.

In yet another embodiment of the present invention, purification of Cetrorelix trifluoroacetate salt (2) was carried out by flash chromatography using a mixture of solvents comprising of ammonium acetate, acetic acid, water, acetonitrile and methanol and optionally converting into pharmaceutically acceptable salt. Finally, the pure Cetrorelix trifluoroacetate salt (2) was converted into a suitable salt, preferably to Cetrorelix hydrochloride or Cetrorelix acetate, more preferably pure Cetrorelix acetate (1), with purity greater than 99.0%.

In another embodiment Cetrorelix acetate (1) obtained after purification is having purity greater than 99.0%.

DETAILED DESCRIPTION

Accordingly, in one embodiment, the present invention provides an improved process which is industrially viable, cost effective for the preparation of Cetrorelix acetate (1) having purity greater than 99.0%.

In another embodiment, the invention provides an improved process for the preparation of Cetrorelix acetate (1) as illustrated in scheme 1, comprising of the following steps:
Scheme-1
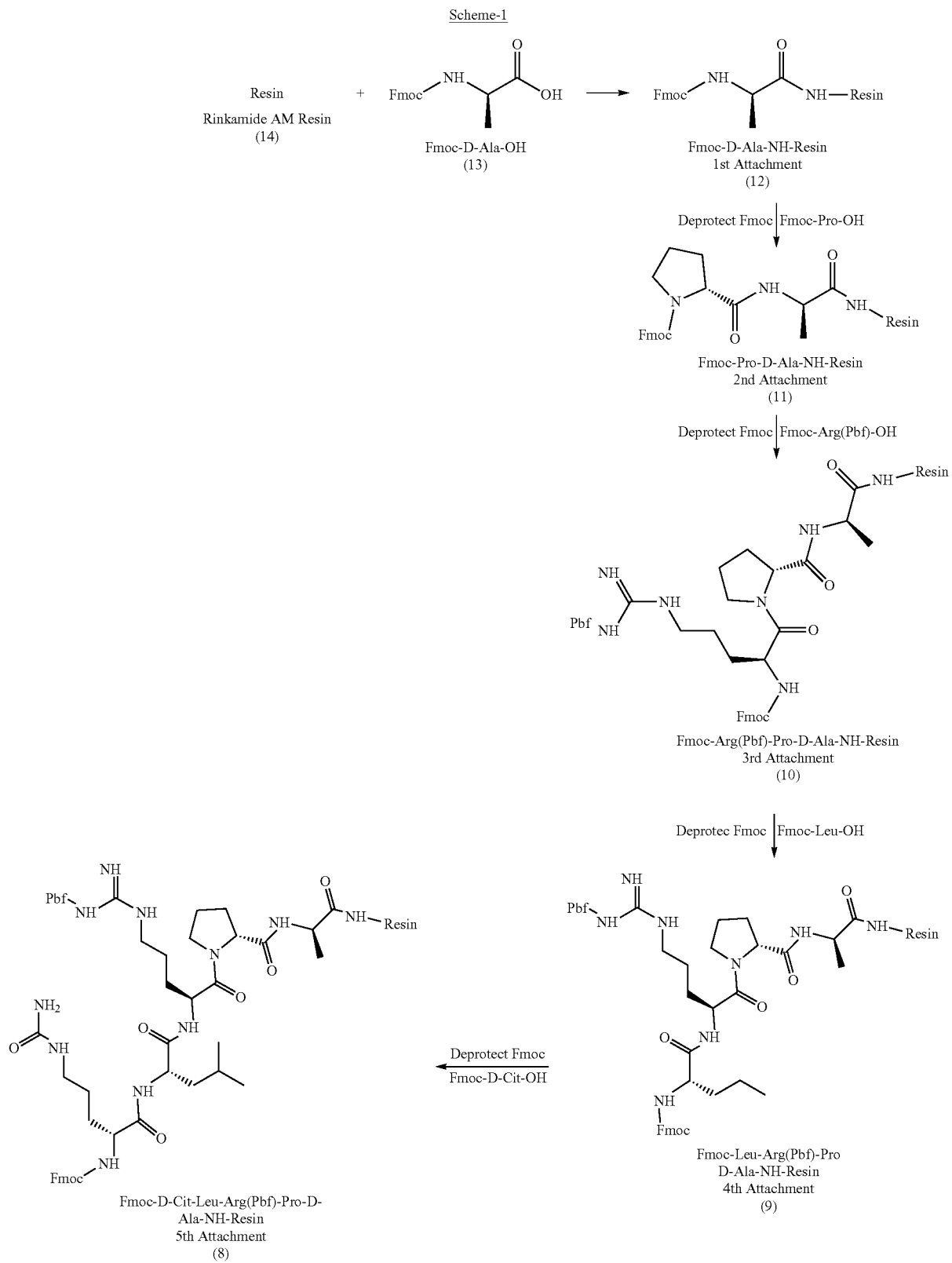

-continued
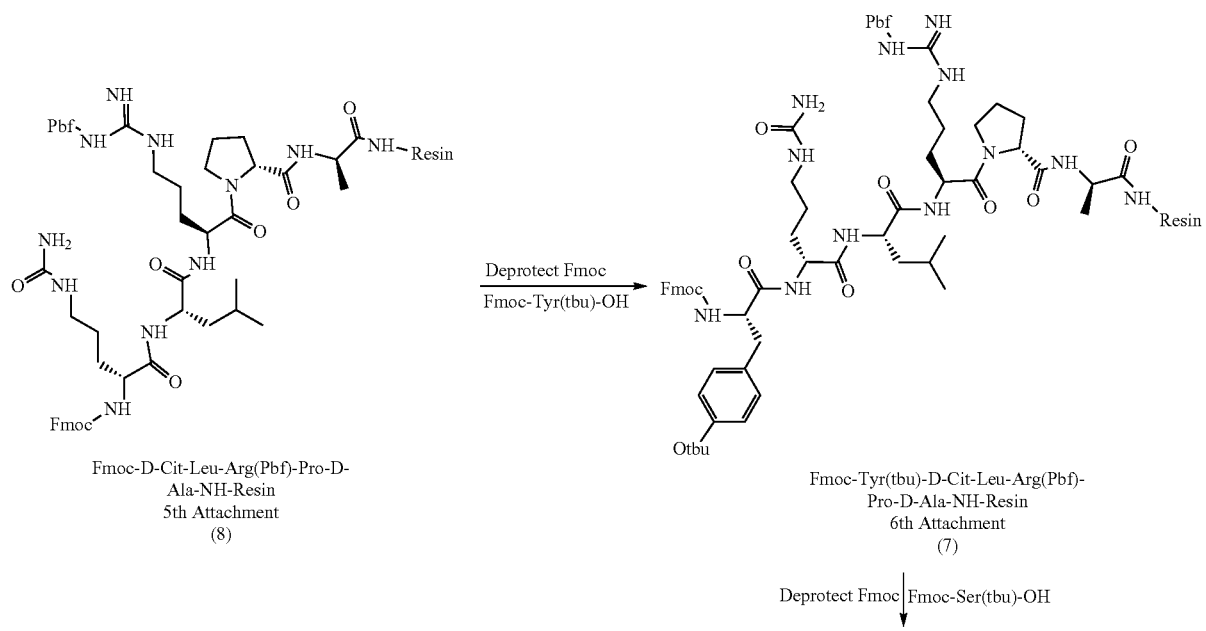
Fmoc-D-Cit-Leu-Arg(Pbf)-Pro-D-
Ala-NH-Resin
5th Attachment
(8)
Fmoc-Tyr(tbu)-D-Cit-Leu-Arg(Pbf)-
Pro-D-Ala-NH-Resin
6th Attachment
(7)
Deprotect Fmoc | Fmoc-Ser(tbu)-OH
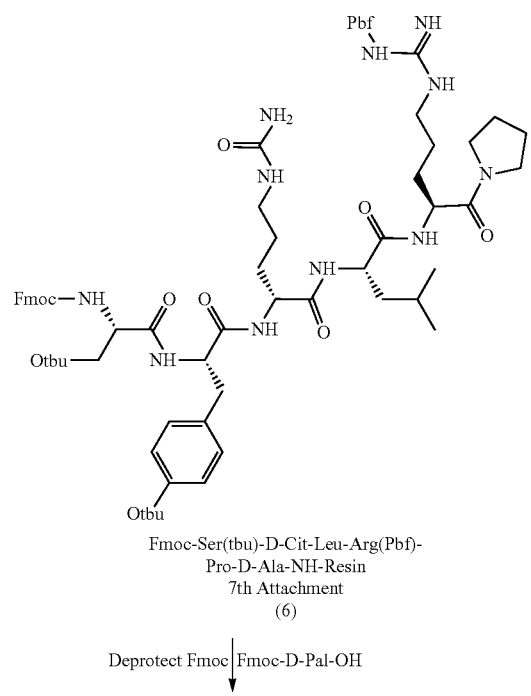
Fmoc-Ser(tbu)-D-Cit-Leu-Arg(Pbf)-
Pro-D-Ala-NH-Resin
7th Attachment
(6)
Deprotect Fmoc | Fmoc-D-Pal-OH

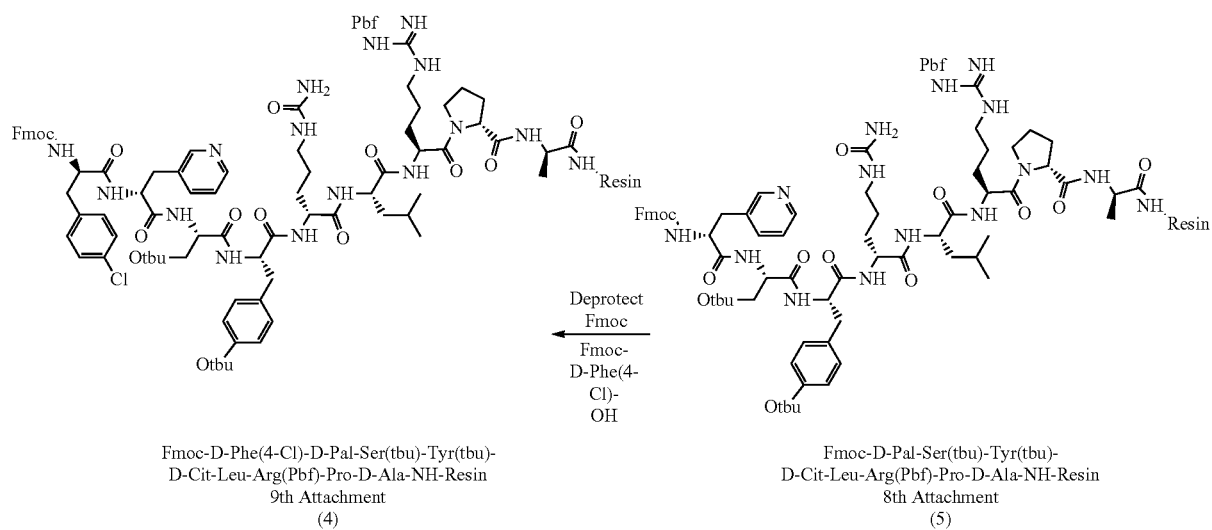
Fmoc-D-Phe(4-Cl)-D-Pal-Ser(tbu)-Tyr(tbu)-
D-Cit-Leu-Arg(Pbf)-Pro-D-Ala-NH-Resin
9th Attachment
(4)
Fmoc-D-Pal-Ser(tbu)-Tyr(tbu)-
D-Cit-Leu-Arg(Pbf)-Pro-D-Ala-NH-Resin
8th Attachment
(5)
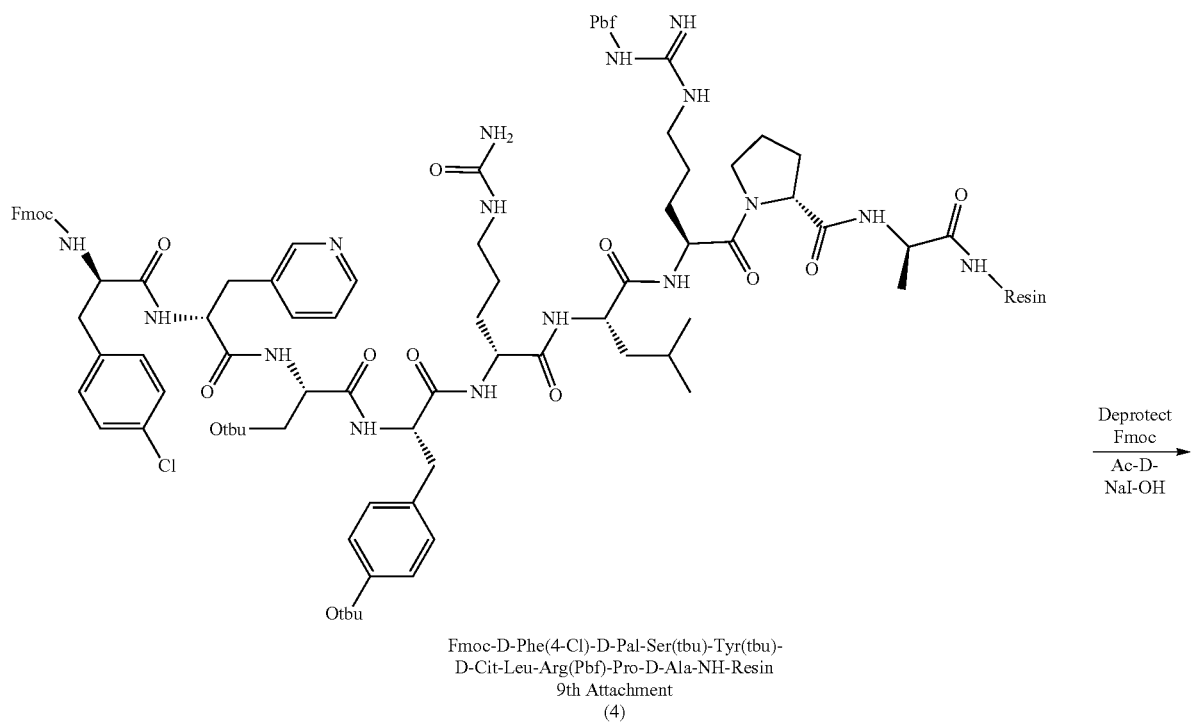
Fmoc-D-Phe(4-Cl)-D-Pal-Ser(tbu)-Tyr(tbu)-
D-Cit-Leu-Arg(Pbf)-Pro-D-Ala-NH-Resin
9th Attachment
(4)

-continued
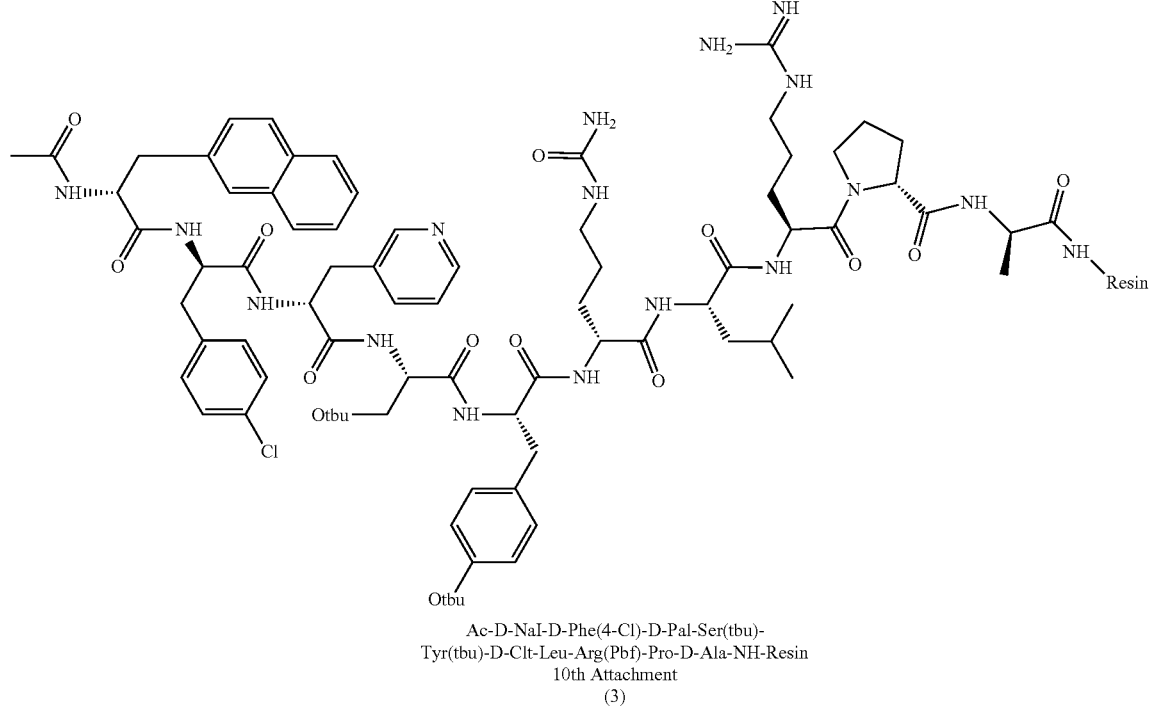
Ac-D-NaI-D-Phe(4-Cl)-D-Pal-Ser(tbu)-
Tyr(tbu)-D-Clt-Leu-Arg(Pbf)-Pro-D-Ala-NH-Resin
10th Attachment
(3)
Purification ↓
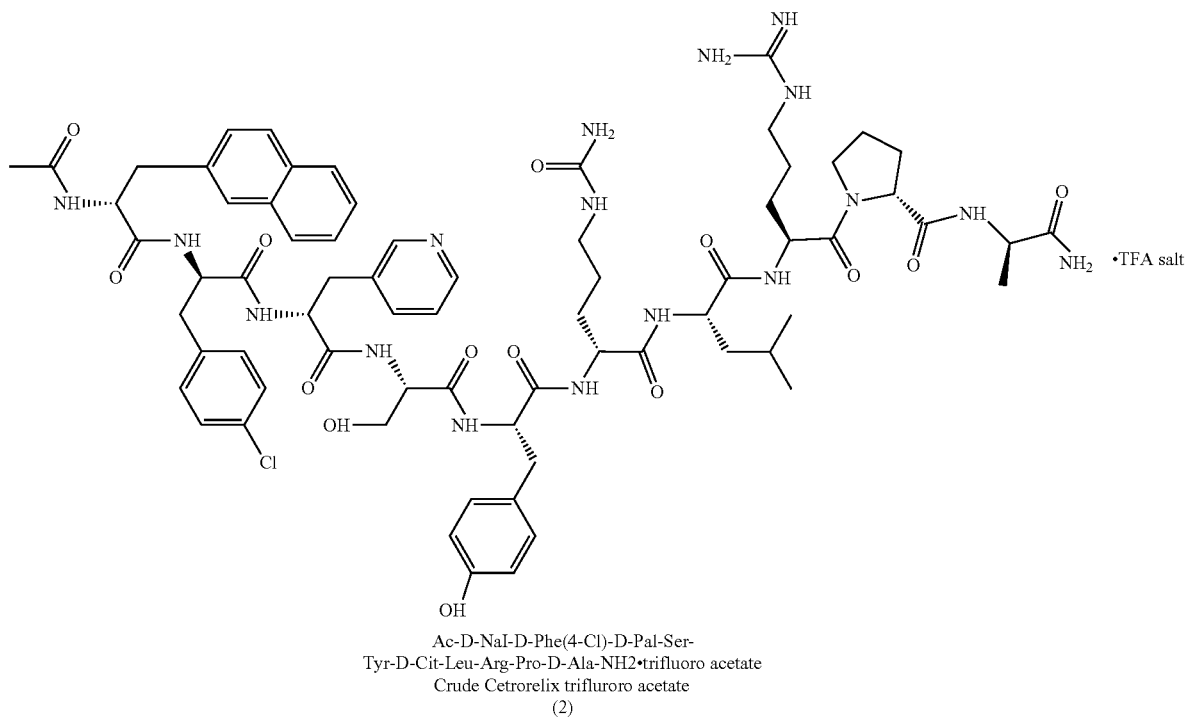
Ac-D-NaI-D-Phe(4-Cl)-D-Pal-Ser-
Tyr-D-Cit-Leu-Arg-Pro-D-Ala-NH2•trifluoro acetate
Crude Cetrorelix trifluoro acetate
(2)
Flash Chromatography | Desalting and salt exchange ↓

-continued

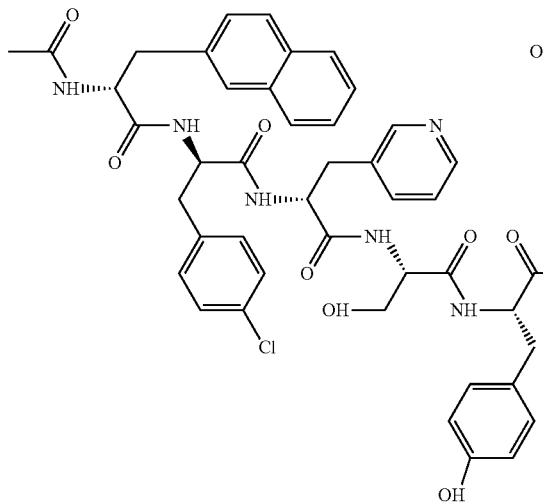
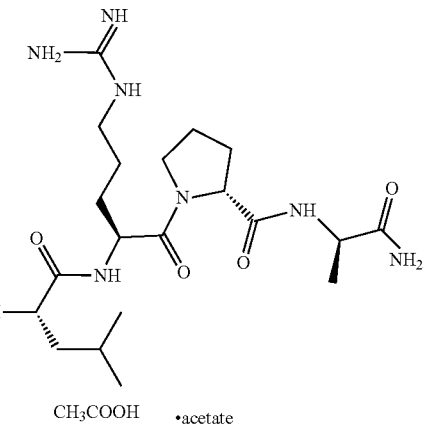

Ac-D-Nal-D-Phe(4-Cl)-D-Pal-Ser-
Tyr-D-Cit-Leu-Arg-Pro-D-Ala-NH2•acetate
Cetrorelix acetate
(1)

a) loading first amino acid Fmoc-D-alanine (13) on Rink amide AM resin (14) to obtain Fmoc-D-Ala-NH-Rink amide resin (12) using manual solid phase synthesizer.

b) deprotecting Fmoc-D-Ala-NH-Rink amide resin (12) and coupling with the required amino acids to form Ac-D-Nal-D-Phe(4-Cl)-D-Pal-Ser(tbu)-Tyr(tbu)-D-Cit-Leu-Arg(Pbf)-Pro-D-Ala-NH-Resin (3), in the said order, wherein the order of amino acids Fmoc-D-alanine, Fmoc-L-proline, Fmoc-D-Arginine(Pbf), Fmoc-L-leucine, Fmoc-D-citruline, Fmoc-O-tert-butyl-L-tyrosine, Fmoc-O-tert-butyl-L-serine, Fmoc-D-3-(3"-pyridyl)-D-alanine, Fmoc-D-4-chlorophenyl alanine, N-acetyl-D-3-(2-naphthyl)alanine to form protected peptide intermediate (3)

c) cleaving protected peptide Ac-D-Nal-D-Phe(4-Cl)-D-Pal-Ser(tbu)-Tyr(tbu)-D-Cit-Leu-Arg (Pbf)-Pro-D-Ala-NH-Resin (3) from the Rink amide AM resin and deprotecting Fmoc protecting group to yield Cetrorelix trifluoroacetate salt (2)

d) purifying Cetrorelix trifluoro acetate (2) by Flash chromatography, to pure Cetrorelix trifluoro acetate (2) with purity more than 99.0% (w/w).

e) isolating Cetrorelix acetate (1) by salt exchange method.

In some embodiment step a) involves loading the first protected amino acid Fmoc-D-Alanine (13) on the suitable resin in a suitable aprotic solvent or mixture thereof.

The suitable resin used in step a) may be selected from a group comprising Rink Amide, Rink Amide AM, Rink Amide MBHA and Seiber amide Resin, preferably Rink amide AM resin was used in the present invention.

In another embodiment, step b) proceeds with the deprotection of the Fmoc group of Fmoc-D-Ala-NH-Rink amide resin (12) using a suitable deprotecting agent and coupling with the next protected amino acids in the following order, wherein the order of amino acids Fmoc-D-alanine, Fmoc-L-proline, Fmoc-D-Arginine(Pbf), Fmoc-L-leucine, Fmoc-D-citruline, Fmoc-O-tert-butyl-L-tyrosine, Fmoc-O-tert-butyl-L-serine, D-3-(3"-pyridyl)-D-alanine, Fmoc-D-4-chlorophenyl alanine, N-acetyl-D-3-(2-naphthyl)alanine to form protected peptide intermediate Ac-D-Nal-D-Phe(4-Cl)-D-Pal-Ser(tbu)-Tyr(tbu)-D-Cit-Leu-Arg(Pbf)-Pro-D-Ala-NH-Resin (3), wherein the hydroxyl groups of L-tyrosine and L-serine and the Nω free amino group were protected with a suitable protecting agent.

In another embodiment, step c) involves cleavage of the peptide from the Rink amide resin and deprotection of the Fmoc side chain protecting group of L-arginine, L-tyrosine and L-serine in a single step to obtain Cetrorelix trifluoro acetate (2)

The deprotecting agents used in step b) may be selected from a group with a mixture of reagents selected from the group comprising of 4 MP (4-methylpiperidine), PP (piperidine), and PZ (piperazine), 1,8-Diazabicyclo[5.4.0]undec-7-ene (DBU), while the side chain deprotection may be carried out using TFA (trifluro acetic acid), TES (Triethyl silane), TIS (Triisopropyl silane), thioanisole, anisole, EDT (Ethanedithiol), phenol, DMS (Dimethyl sulfide), p-cresol and m-cresol, preferably PP (piperidine) and pyridine were used herein. While step c) preferably involves use of TFA (trifluro acetic acid), and TIS (Triisopropyl silane).

In another embodiment, the hydroxyl protecting group may be selected from groups comprising DMT (dimethoxy trityl), MMT (Methoxytrityl), TRT (Trityl), tert-butyl, t-butoxy carbonyl and the like; preferably tert-butyl was used in the present invention.

The amino protecting group may be selected from group comprising Fmoc (9-fluorenyl methoxy carbonyl), Boc (tert-butyloxycarbonyl), Cbz (Benzyloxycarbonyl), Bpoc (2-(4-biphenyl)-2-propyloxycarbonyl), 2,2,4,6,7-pentamethyldihydrobenzofuran-5-sulfonyl (Pbf) or the like. Preferably Fmoc (9-fluorenyl methoxy carbonyl) was used in the present invention and 2,2,4,6,7-pentamethyldihydrobenzofuran- 5-sulfonyl (Pbf) was specifically used for the protection of Nω free amino group of L-arginine.

The said coupling agent (s) used in step (b) above may be selected from the group consisting of phosgene, carbonyldiimidazole (CDI), HOBt (Hydroxy benzotriazole), TBTU (0-(benzotriazol-1-yl)-N,N,N',N'-tetramethyluronium tetrafluoroborate), DCC (1,3-dicyclohexylcarbodiimide), DIC (Diisopropylcarbodiimide), HBTU (O-Benzotriazole-N,N, N'N-tetramethyluronium hexafluoro phosphate), BOP (Benzotriazol-I-yl-oxy-tris(dimethylamino)phosphonium hexafluorophosphate), PyBOP (Benzotriazol-1-yloxy tri (pyrrolidino)phosphonium hexafluorophosphate), PyBrOP (Bromotri(pyrrolidino)phosphonium hexafluorophosphate), Chlorotri(pyrrolidino)phosphonium hexafluorophosphate (PyClOP), Ethyl-2-cyano-2-(hydroxyimino) acetate (Oxyma Pure), 0-(6-Chlorobenzotriazol-I-yl)-I,I,3,3-tetramethyluronium tetrafluoroborate (TCTU), Ethyl 1,2-dihydro-2-ethoxyquinoline-I-carboxylate(EEDQ),1-Cyano-2-ethoxy-2oxoethyHdenaminooxy)dimethylaminomorpholino carbenium hexafluorophosphate (COMU), 3-(Diethoxy-phosphoryloxy)-3H-benzo[d][1,2,3] triazin-4-one (DEPBT), 1-hydroxy 7-azabenzotriazole (HoAt), 1-[Bis(dimethylamino)methylene]-1H-1,2,3-triazolo[4,5-b]pyridinium 3-oxidhexafluoro phosphate (HATU), dimethylamino(triazolo[4,5-b]pyridin-3-yloxy)methylidene]-dimethylazanium tetra fluoroborate (TATU) and the like, and mixtures thereof; preferably the coupling agent used was DIC (Diisopropylcarbodiimide) and HOBt (Hydroxy benzotriazole).

The coupling reaction in step (b) above may be carried out in presence of solvents selected from the group comprising of N,N-dimethylformamide (DMF), dichloromethane (DCM), tetrahydrofuran (THF), N-methyl pyrrolidine (NMP), dimethylacetamide (DMAC) or mixtures thereof; preferably the solvent used in step (b) was N,N-dimethylformamide and dichloromethane or mixture thereof.

In another embodiment, the aprotic solvents used in the present invention may be selected from a group comprising of acetone, acetonitrile, 1,4-dioxane, diethyl ether, dichloromethane (DCM), dimethyl sulfoxide (DMSO), ethyl acetate, N,N-dimethylformamide (DMF), methyl tertiary butyl ether (MTBE), hexane, cyclohexane, toulene, n-methyl pyrrolidone, Dimethyl acetamide, tetrahydrofuran or the like, preferably acetonitrile, dimethylformamide, dichloromethane dimethyl sulfoxide and methyl tertiary butyl ether (MTBE) were used in the present invention.

In yet another embodiment, step d) involves purifying crude Cetrorelix trifluoro acetate (2) by Flash chromatography, to pure Cetrorelix trifluoro acetate (2) having purity more than 99.0% comprising:
  I. mixing Cetrorelix trifluoroacetate salt (2) in a suitable diluent;
  II. eluting the sample through cartridge; and
  III. isolating pure Cetrorelix trifluoroacetate salt (2).

Purification of crude Cetrorelix trifluoroacetate salt (2) may be carried out by flash chromatography, which involves charging Cetrorelix trifluoroacetate salt (2) in a suitable diluent and sonicating the reaction mixture for 5 mins, followed by injecting the sample into the cartridge manually and isolating pure Cetrorelix as its trifluoroacetate salt (2).

In some embodiment, the crude peptide obtained was added to a suitable diluent and sonicated till it dissolved. The flash cartridges were equilibrated with mobile phase A and B. Mobile A may be comprising of ammonium acetate and maintain the pH at a range of 2 to 4, preferably at 3.8 with an suitable acid and mobile phase B may comprise of a mixture of protic and aprotic solvents, preferably acetonitrile and water in the ratio of 50:50 was used in the present invention. The acid used in mobile phase A may be selected from organic or inorganic acids, preferably organic acids comprising of trifluoroacetic acid (TFA), o-phosphoric acid (OPA), ammonium acetate buffer or the like, more preferably trifluoroacetic acid TFA in mixture of acetic acid and water was used in the present invention.

The prepared sample was then loaded, different fractions were collected and checked for purity. All the fractions having purity more than 98.0% were collected and distilled off. The concentrated mass was then lyophilized to yield Cetrorelix trifluoroacetate salt (2) with purity more than 99.0% by flash chromatography.

In another embodiment the protic solvents used in the above purification process may be selected from a group comprising of water, methanol, ethanol, isopropyl alcohol or the like, preferably water was used in the present invention. Aprotic solvents were selected from a group comprising of acetone, acetonitrile, nitromethane, 1,4-dioxane, diethyl ether, dichloromethane, dimethyl sulfoxide, ethyl acetate, N, N-dimethylformamide, methyl tertiary butyl ether, hexane, butyl acetate cyclohexane, toulene, tetrahydrofuran or the like, preferably acetonitrile and dimethyl sulfoxide were used in the present invention.

The suitable diluent used step I) of purification process of crude Cetrorelix trifluoroacetate salt (2) was selected from the group consisting of water, acetone, N, N-dimethylformamide, dimethyl sulfoxide, (DMSO), alcohol such as methanol, ethanol and isopropanol and/or mixtures thereof. Preferably, dimethyl sulfoxide was used in the present invention.

The cartridge used herein may be selected from a group comprising of reverse phase (C18) cartridges preferably C18 Reveleris reverse phase 120 g, or 330 g with 40 µm particle size was used in the present invention.

The purification was preferably carried out at a column temperature from 10-40° C., preferably 25-30° C. was used in the present invention.

The column pressure should be between 20-70 psi preferably 35-65 psi was used in the present invention.

In some embodiment, step e) of the present invention relates to a process of converting the pure the Cetrorelix trifluoroacetate salt (2) obtained after flash chromatography to the desired pharmaceutically acceptable salt, preferably Cetrorelix acetate salt (1) by Cetrorelix desalting and slat exchange process using suitable resin and suitable acid. Pure Cetrorelix trifluoroacetate salt (2) may be dissolved in a mixture of suitable solvents and pH at a range maintained at 10 to 11, preferably at a range of 10.3 to 10.5 using a suitable basic resin, preferably Indion-810 was used in the present invention. The resin may be removed by filtration and a suitable acid based on the desired pharmaceutically acceptable salt may be added to the reaction mass preferably glacial acetic acid was used. The reaction mass was filtered and pure Cetrorelix was isolated as its pharmaceutically acceptable salt form, preferably as Cetrorelix as acetate salt (1). The present invention is advantageous over other the prior art, as the present invention avoids the use of any type of chromatography for the isolation of pure Cetrorelix as acetate salt (1), which makes the present process simple, economic and also results in good yield.

The suitable basic resins used for salt exchange in step e) may be selected from a group comprising of (Indion-810 resin), PolyAPTAC, or poly (acrylamido-N-propyltrimethylammonium chloride) and PolyMAPTAC, or poly[(3-

(methacryloylamino)-propyl] trimethylammonium chloride), preferably Indion-810 resin was used in the present invention.

In some embodiment, the pure Cetrorelix acetate (1) obtained after purification may be having purity more than 99.0% (w/w).

In another embodiment, pure Cetrorelix acetate (1) obtained after purification may be having unknown single maximum impurity less than 0.1 (% w/w) and total impurities less than 1.0 (% w/w), more specifically 0.4 (% w/w).

In another embodiment, Cetrorelix acetate obtained in the present invention is having each impurity A, impurity B, impurity C and impurity D less than 1.0% (w/w) and more preferably impurity each impurity A, B, C and D are less than 0.5% (w/w).

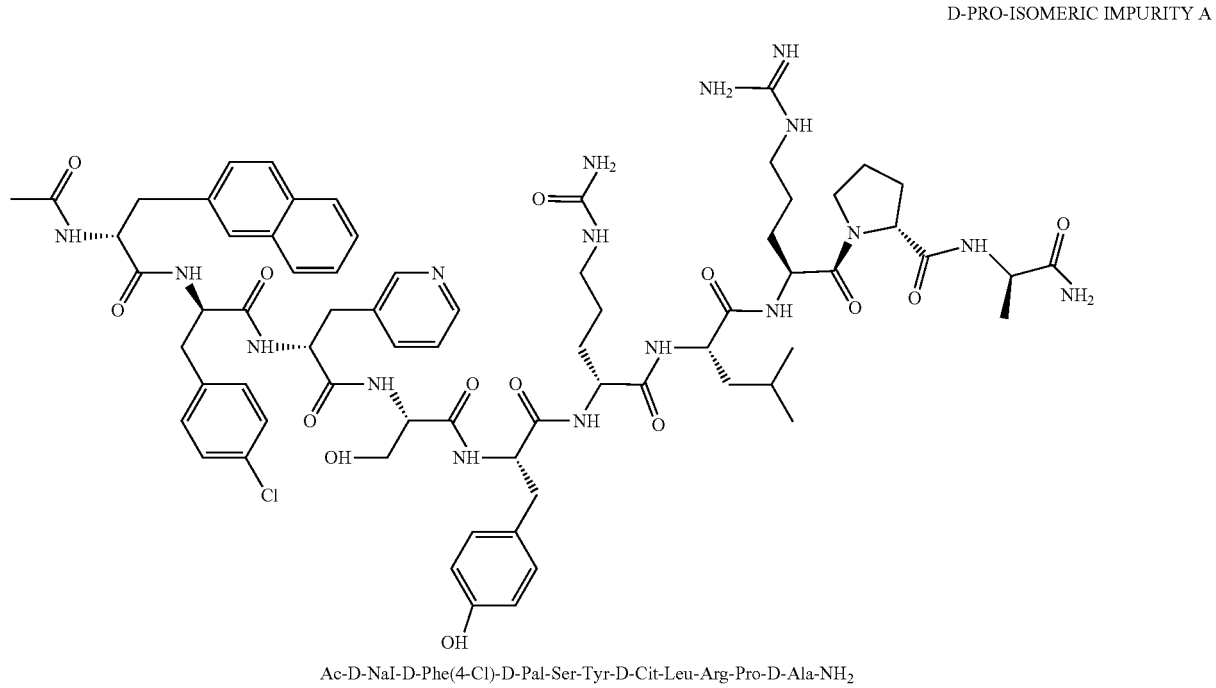

Ac-D-NaI-D-Phe(4-Cl)-D-Pal-Ser-Tyr-D-Cit-Leu-Arg-Pro-D-Ala-NH$_2$

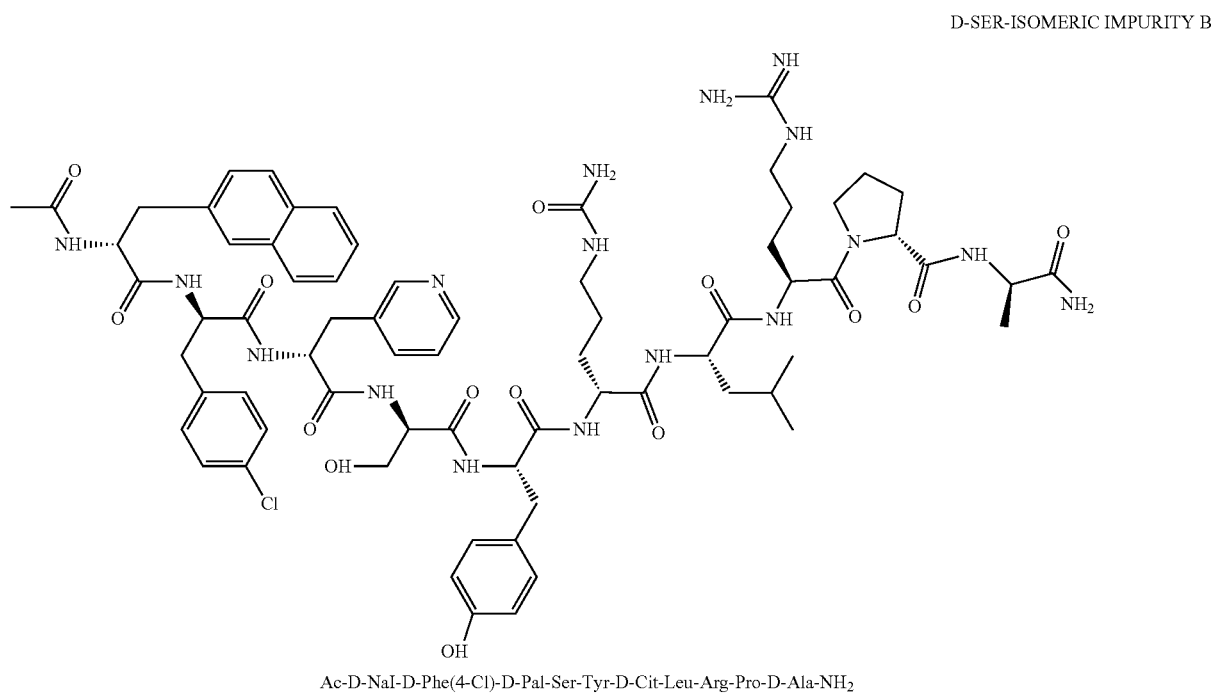

Ac-D-NaI-D-Phe(4-Cl)-D-Pal-Ser-Tyr-D-Cit-Leu-Arg-Pro-D-Ala-NH$_2$

-continued

L-PHENYLALANINE (4-Cl) ISOMERIC IMPURITY C

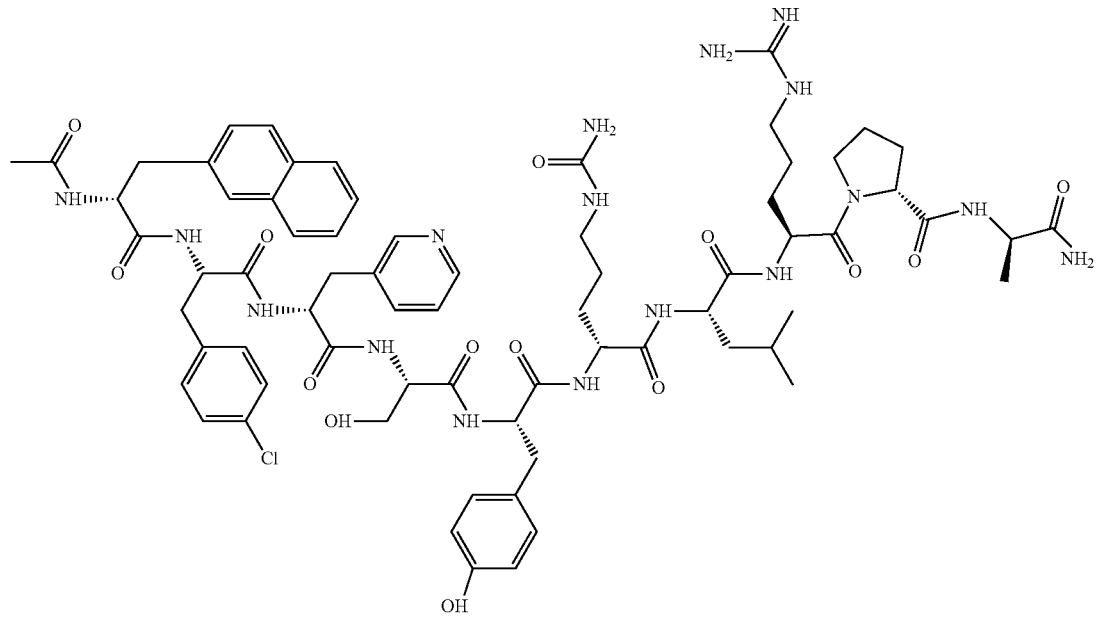

Ac-D-NaI-L-Phe(4-Cl)-D-Pal-Ser-Tyr-D-Cit-Leu-Arg-Pro-D-Ala-NH$_2$ 1-7 ACID IMPURITY D

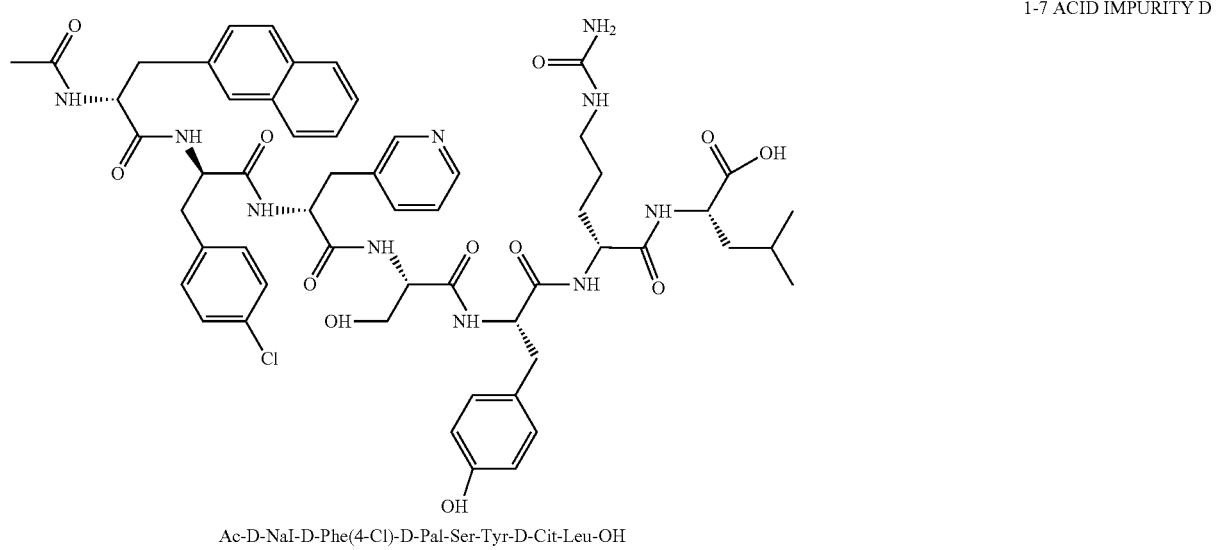

Ac-D-NaI-D-Phe(4-Cl)-D-Pal-Ser-Tyr-D-Cit-Leu-OH

In another embodiment the water content of pure Cetrorelix acetate (1) by Karl Fischer method was less than 10.0 (% w/w).

In yet another embodiment, the present invention provides pure Cetrorelix acetate (1), having total heavy metals level less than 10 ppm and a specific rotation between −20° and −30°.

BRIEF DESCRIPTION OF ABBREVIATIONS

| | |
|---|---|
| HOAt | 1-hydroxy 7-azabenzotriazole |
| HOBt | Hydroxy benzotriazole |
| Cl—HOBt | 6-chloro 1-hydroxy-benzotriazole |
| TBTU | O-(benzotriazol-1-yl)-N,N,N',N'-tetramethyluronium tetrafluoroborate, |
| HBTU | O-Benzotriazole-N.N. N' N-tetramethyluroniumhexafluoro phosphate |
| DCC | 1,3-dicyclohexylcarbodiimide |
| DIC | Diisopropylcarbodiimide |
| BOP | Benzotriazol-l-yl-oxy-tris(dimethylamino) phosphonium hexafluorophosphate |
| PyBOP | Benzotriazol-1-yl oxy tri(pyrrolidino)phosphonium hexafluorophosphate |
| PyBrOP | Bromotri(pyrrolidino)phosphonium hexafluorophosphate |
| PyClOP | Chlorotri(pyrrolidino)phosphonium hexafluorophosphate (PyClOP),Oxyma-Ethyl-2-cyano-2-(hydroxyimino) acetate (Oxyma Pure), |
| TATU | [dimethylamino(triazolo[4,5-b] pyridin-3-yloxy) methylidene]-dimethylazanium tetra fluoroborate |
| TCTU | 2-(1H-Benzotriazole-1-yl)-1,1,3,3-tetramethyluronium tetrafluoro borate |

-continued

| | |
|---|---|
| HATU | 1-[Bis(dimethylamino)methylene]-1H-1,2,3-triazolo[4,5-b]pyridinium 3-oxid hexa fluorophosphate |
| EEDQ | Ethyl 1,2-dihydro-2-ethoxyquinoline-l-carboxylate |
| COMU | 1-Cyano-2-ethoxy-2-oxoethylidenaminooxy) dimethylamino morpholino carbenium hexafluorophosphate |
| Oxyma | ethyl 2-cyano-2-(hydroxyimino)acetate |
| DIPEA | N,N-diisopropylethylamine (DIEA) |
| DMF | N,N-dimethylformamide |
| DCM | Dichloromethane |
| THF | Tetrahydrofuran |
| NMP | N-Methyl pyrrolidine |
| DMAc | Dimethylacetamide |
| TFA | Trifluoro acetic acid |
| EDT | Ethanedithiol |
| TIS | Triisopropyl silane |
| TES | Triethyl silane |
| DTT | Diothreitol |
| DMS | Dimethyl sulfide |
| DMSO | Dimethyl sulfoxide |
| MTBE | Methyl tert-butylether |
| MeOH | Methanol |
| IPA | Isopropyl alcohol |
| RAAM | Rink Amide Amino methyl |
| Trt | Trityl |
| Acm | Acetamidomethyl |
| StBu | S-tert-butylmercapto |
| Tmob | Trimethoxybenzyl |
| (Pbf) | 2,2,4,6,7-pentamethyldihydrobenzofuran-5-sulfonyl |
| DMT | dimethoxy trityl |
| MMT | Methoxytrityl |
| Fmoc | 9-fluorenyl methoxycarbonyl |
| Boc- | tert-butoxycarbonyl |
| Cbz | Benzyloxycarbonyl |
| Bpco | 2-(4-biphenyl)-2-propyloxycarbonyl |
| TACM | S-Trimethylacetamidomethyl |
| DEPBT | 3-(Diethoxy-phosphoryloxy)-3H-benzo[d][1,2,3] triazin-4-one |

The following examples further illustrate the present invention, but should not be construed in anyway, as to limit its scope.

EXAMPLES

Example-1: Preparation of Fmoc-D-Ala-NH-Rink Amide Resin (12) 100 g of Rink Amide AM Resin was Suspended to Swell in 1000 mL of Dimethylformamide at 25-30° C. for 3-4 Hrs Under Slow Stirring The solvent was then removed under vacuum. The dried resin was then treated with 500 mL of 20% piperidine in dimethyl formamide for 10-15 min at 25-30° C. and dried under vacuum. Further, the resin so obtained was treated alternatively with 500 mL of dimethyl formamide and 500 mL of dichloromethane several times and dried under vacuum.

In another clean and dry round bottom flask, 70 g of Fmoc-D-Ala-OH was dissolved in 400 mL of dimethylformamide at 25-30° C. and 30 g of HOBt was added. The reaction mixture was cooled to 0-5° C. and stirred for 10-15 mins. 55 mL of N, N'-diisopropylcarbodiimide (DIC) was then added to the reaction mixture at 0-5° C.

The activated amino acid (Fmoc-D-Ala-OH) solution was then added to the dried Rink amide AM resin and stirred for 2-3 hrs at 25-30° C. On completion of reaction, 600 mL of dimethyl formamide was added to the reaction mass and stirred for 5-10 min at 25-30° C. The total reaction mass was dried under vacuum and the residue was treated with 600 mL of dichloromethane and dried under vacuum at 25-30° C. The same process was followed with 600 mL of dimethyl formamide and the solvent removed under vacuum.

The residue so obtained was then treated with 500 mL of dimethylformamide, acetic anhydride and pyridine mixture and dried under vacuum. The dried resin was then treated with 600 mL of dimethyl formamide, stirred for 10-15 mins and dried under vacuum. Further, the same process was repeated with 600 mL of dichloromethane followed by 600 mL of dimethyl formamide to obtain the dried resin of Fmoc-D-Ala-NH-Rink amide resin (12).

Example-2: Preparation of Protected Peptide-Rink Amide Resin (3)

The Fmoc-D-Ala-NH-Rink amide resin (12) was treated with 600 mL of 20% in piperidine in dimethyl formamide at 25-30° C. temperature. The reaction mass was stirred for 10-15 min and solvent was removed under vacuum. The residue was treated again with 600 mL of 20% in piperidine in dimethyl formamide at 25-30° C. To this amino acids were coupled in the said order, wherein the order of amino acids was Fmoc-D-alanine, Fmoc-L-proline, Fmoc-D-Arginine(Pbf), Fmoc-L-leucine, Fmoc-D-citruline, Fmoc-O-tert-butyl-L-tyrosine, Fmoc-O-tert-butyl-L-serine, D-3-(3"-pyridyl)-D-alanine, Fmoc-D-4-chlorophenyl alanine, N-acetyl-D-3-(2-naphthyl)alanine by using Hydroxybenzotriazole (HoBt) and Diisopropylcarbodiimide (DIC) to form Ac-D-Nal-D-Phe(4-CI)-D-Pal-Ser(tbu)-Tyr(tbu)-D-Cit-Leu-Arg(Pbf)-Pro-D-Ala-NH-Resin (3). Optionally, capping solution comprising of acetic anhydride, pyridine, dichloromethane and dimethyl formamide was added to the resin, stirred for 15 mins and filtered in each step.

Example-3: Preparation of Cetrorelix Trifluoroacetate Salt (2)

100 g of the intermediate Ac-D-Nal-D-Phe(4-CI)-D-Pal-Ser(tbu)-Tyr(tbu)-D-Cit-Leu-Arg (Pbf)-Pro-D-Ala-NH-Resin (3) so obtained was added to the cleavage cocktail at 0-5° C. The cleavage cocktail was prepared using 1100 mL of trifluoro acetic acid, 25 mL of triisopropylsilane and 25 mL of water at 25-30° C. and cooled to 0-5° C. The reaction mass was kept undisturbed for 1-2 h at 25-30° C. On completion of the reaction, the 50% of the trifluoro acetic acid was removed by distillation using rotavapor under vacuum. The reaction mixture with remaining 50% solvent was added to methyl tertiary butyl ether at 0-5° C., stirred for 1-2 hrs and filtered under vacuum. The process was repeated 3-4 times and finally the obtained solid was washed with methyl tertiary butyl ether and dried under vacuum at 25-30° C. to obtain Cetrorelix trifluoroacetate salt (2). Yield: 80.0 gms. Purity: 75%.

Example-4: Purification of Cetrorelix Trifluoroacetate Salt (2)

The Flash chromatography was inspected for cleanliness. The three cartridges were connected to the Flash chromatography system. 15 mL of dimethyl sulfoxide was added to 5.0 g of the Cetrorelix trifluoroacetate salt (2) and sonicated. The sample thus prepared was injected into the Flash cartridge manually. The cartridges were first equilibrated for 20 minutes with mobile phase A and mobile phase B. Mobile phase A consisted of 0.02M ammonium acetate and adjust the pH 3.8±0.05 with trifluoracetic acid and mobile phase B was a mixture of acetonitrile and water in the ratio of 50:50). The sample was loaded to the cartridges by manually and chromatography was carried out according to the following gradient program (50:50 acetonitrile: water) and the chromatographic conditions tabulated below:

Chromatographic Conditions:
Instrument: Grace Flash Chromatography system with UV detector, data handling system
Flash: C18 Reveleris reverse phase silica 120 g, 40 μm, 320 g,
Cartridge 40 μm
Wavelength: 210, 220 nm
Flow Rate: 50 mL/minute
Run time: 130 minutes
Diluent: Dimethyl sulfoxide (DMSO)
Preparation of Mobile phases:
Mobile phase: 0.02M Ammonium Acetate and adjust the pH 3.8
A ±0.05 with TFA
Mobile phase: Mixture of Acetonitrile and Water in the ratio of 50:50.
B
Injection load: 5.0 g/injection
Retention time: 55-75 min
Gradient Program:

| Time | Mobile phase-A % | Mobile phase-B % |
|------|------------------|------------------|
| 0    | 90               | 10               |
| 5    | 90               | 10               |
| 25   | 30               | 70               |
| 25   | 30               | 70               |
| 5    | 25               | 75               |
| 30   | 25               | 75               |
| 10   | 10               | 90               |
| 20   | 0                | 100              |

The eluent flow is 50 mL/minute, column or cartridge pressure of around 65 psi being built up in each case depending on the gradient conditions. The peak detection was performed in UV light at 210 nm/220 nm, manually. The peak at between 55-75 mins retention time (RT) were collected and simultaneously the purity of test tubes getting absorbance between peak start 1.50 AU to peak end 0.76 AU by HPLC were checked and proceed for next lot. All the Flash test tubes of HPLC purity having >98.5% were collected and mixed in a clean and dry RB flask. The fractions were distilled off to remove acetonitrile from the solution under vacuum below 30° C. The concentrated mass was collected and then lyophilized to obtain the Cetrorelix trifluoroacetate salt (2). Yield: 20%; Purity: 98%

Example-5: Isolation of Pure Cetrorelix Acetate by Salt Exchange Process

The Cetrorelix trifluoroacetate salt (2) was mixed with 300 volumes of mixture of methanol: water (1:1) and stirred at 25-30° C. A basic resin Indion-810 was then added and the pH was adjusted to 10.3-10.5 for 1 hr. The resin was then filtered. The basic resin was added again to the filtrate and adjusted pH to 10.3-10.5 then stirred for 30 mins and trifluoracetic acid limit was determined. On complying the limit, 0.6-0.7 volume (weight of the Cetrorelix TFA salt) of glacial acetic acid was added to the reaction solution, stirred for 30 mins, and filtered through 0.45-micron filter. The filtrate was lyophilized for 48-52 hrs to obtain pure Cetrorelix acetate (1). Yield: 85.0%; Peptide Purity: 99.6%; Acetate content: 3.6-7.9%.

While the present disclosure has been illustrated and described with respect to a particular embodiment thereof, it should be appreciated by those of ordinary skill in the art that various modifications to this disclosure may be made without departing from the spirit and scope of the present disclosure.

What is claimed is:

1. A process for the preparation of Cetrorelix acetate

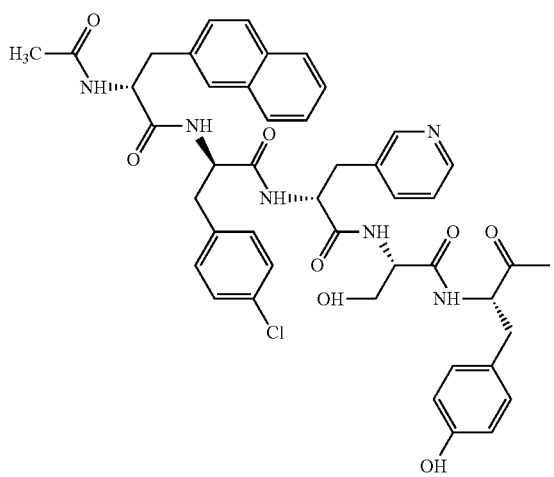

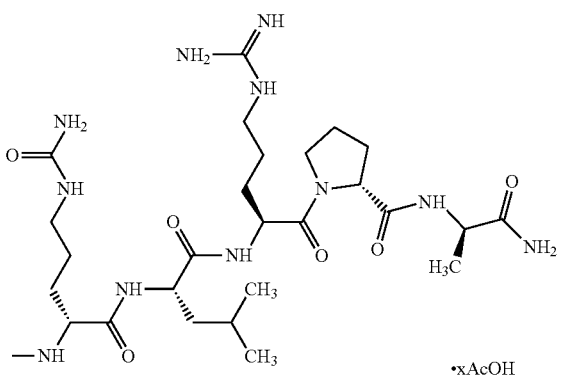

Ac-D-NaI-D-p-Cl-Phe-D-PaI-Ser-Tyr-D-Cit-Leu-Arg-Pro-D-Ala-NH$_2$
Cetrorelix acetate comprising:
a) loading first protected amino acid Fmoc-D-Alanine (13)

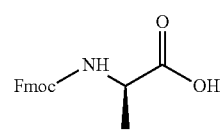

Fmoc-D-Ala-OH on a suitable acid sensitive resin to obtain intermediate

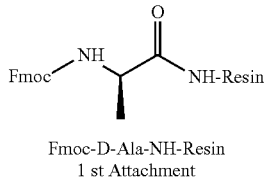

Fmoc-D-Ala-NH-Resin
1 st Attachment (12)

using solid phase synthesizer;
b) deprotecting the Fmoc group of intermediate and coupling intermediate with the required amino acids using a suitable coupling agent in the said order, wherein the order of amino acids are Fmoc-D-alanine, Fmoc-L-proline, Fmoc-D-Arginine(Pbf), Fmoc-L-leucine, Fmoc-D-citruline, Fmoc-O-tert-butyl-L-tyrosine, Fmoc-O-tert-butyl-L-serine, D-3-(3'-pyridyl)-D-alanine, Fmoc-D-4-chlorophenyl alanine, N-acetyl-D-3-(2-naphthyl)alanine to form protected peptide intermediate;

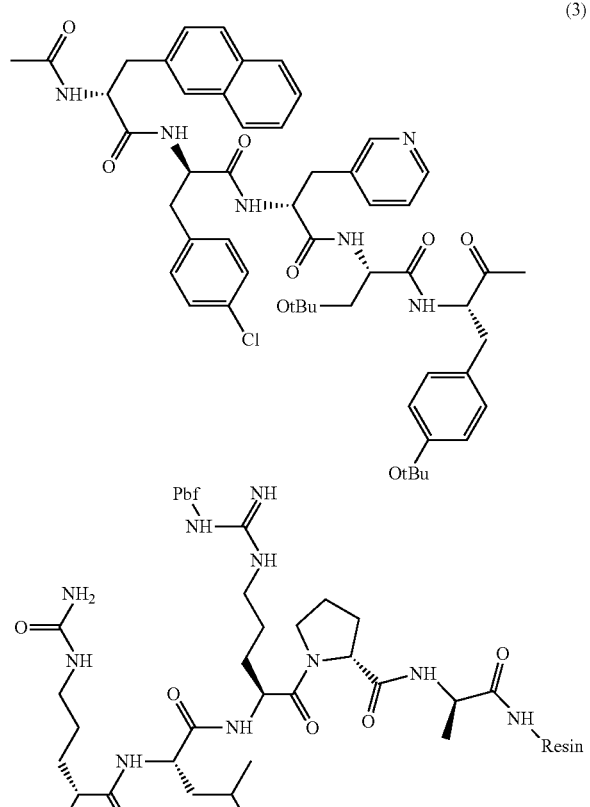

Ac-D-Nal-D-Phe(4-Cl)-D-Pal-Ser(tbu)-
Tyr(tbu)-D-Cit-Leu-Arg(Pbf)-Pro-D-Ala-NH-Resin
10th Attachment (3)

c) cleaving protected peptide intermediate from the resin and deprotecting the side chain protecting groups to yield Cetrorelix trifluoro acetate;

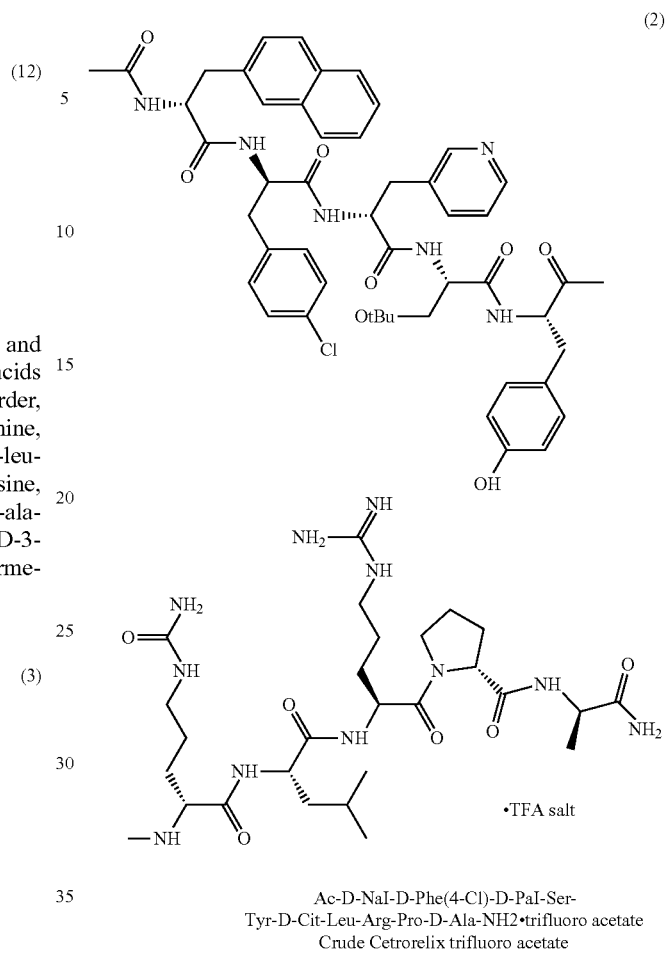

Ac-D-Nal-D-Phe(4-Cl)-D-Pal-Ser-
Tyr-D-Cit-Leu-Arg-Pro-D-Ala-NH2•trifluoro acetate
Crude Cetrorelix trifluoro acetate (2)

d) purifying Cetrorelix trifluoro acetate by Flash chromatography;
e) converting Cetrorelix trifluoro acetate to Cetrorelix acetate by salt exchange method to obtain pure Cetrorelix acetate.

2. The process as claimed in claim 1, wherein the amino protecting group is selected from group comprising of Fmoc (9-fluorenyl methoxy carbonyl), Boc (tert-butyloxycarbonyl), Cbz (Benzyloxycarbonyl), Bpoc (2-(4-biphenyl)-2-propyloxycarbonyl), 2,2,4,6,7-pentamethyldihydrobenzofuran-5-sulfonyl (Pbf).

3. The process as claimed in claim 1, wherein the hydroxyl protecting group is selected from the group comprising of DMT (dimethoxy trityl), MMT (Methoxytrityl), TRT (Trityl), tert-butyl, t-butoxy carbonyl.

4. The process as claimed in claim 1, wherein the coupling agent (s) is selected from the group comprising of phosgene, carbonyldiimidazole (CDI), HOBt (Hydroxy benzotriazole), TBTU (0-(benzotriazol-1-yl)-N,N,N',N'-tetramethyluronium tetrafluoroborate), DCC (1,3-dicyclohexylcarbodiimide), DIC (Diisopropylcarbodiimide), HBTU (O-Benzotriazole-N,N,N' N-tetramethyluronium hexafluoro phosphate), BOP (Benzotriazol-I-yl-oxy-tris(dimethylamino)phosphonium hexafluorophosphate), PyBOP (Benzotriazol-1-yloxy tri(pyrrolidino)phosphonium hexafluorophosphate), PyBrOP (Bromotri(pyrrolidino)phosphonium hexafluorophosphate), Chlorotri(pyrrolidino)phosphonium hexafluorophosphate (PyClOP), Ethyl-2-cyano-2-(hydroxyimino)

acetate (Oxyma Pure), O-(6-Chlorobenzotriazold-yl)-1,1,3,3-tetramethyluronium tetrafluoroborate (TCTU), Ethyl 1,2-dihydro-2-ethoxyquinoline-1-carboxylate(EEDQ),1-Cyano-2-ethoxy-2oxoethyHdenaminooxy)dimethylamino morpholino carbenium hexafluorophosphate (COMU), 3-(Diethoxy-phosphoryloxy)-3H-benzo[d][1,2,3] triazin-4-one (DEPBT), 1-hydroxy 7-azabenzotriazole (HoAt), 1-[Bis(dimethylamino)methylene]-1H-1,2,3-triazolo[4,5-b]pyridinium 3-oxidhexafluoro phosphate (HATU), dimethylamino(triazolo[4,5-b]pyridin-3-yloxy)methylidene]-dimethylazanium tetra fluoroborate (TATU) or mixtures thereof.

5. The process as claimed in claim 1, wherein the deprotecting agent used is selected from a group comprising of 4 MP (4-methylpiperidine), PP (piperidine), and PZ (piperazine), pyridine, 1,8-Diazabicyclo[5.4.0]undec-7-ene (DBU), TFA (trifluro acetic acid), TES (Triethyl silane), TIS (Triisopropyl silane), thioanisole, anisole, EDT(Ethanedithiol), phenol, DMS (Dimethyl sulfide), p-cresol, m-cresol or mixtures thereof.

6. A process for the purification of Cetrorelix trifluoroacetate with purity greater than 99.0% by Flash chromatography, which comprises of:
    I. mixing Cetrorelix trifluoroacetate salt in a suitable diluent;
    II. eluting the sample through cartridge; and
    III. isolating pure Cetrorelix trifluoroacetate salt.

7. The process as claimed in claim 6, wherein the buffer used is selected from trifluoroacetic acid (TFA), o-phosphoric acid (OPA), ammonium acetate buffer or mixtures thereof.

8. A process for the preparation of Cetrorelix acetate with purity greater than 99.0% by converting Cetrorelix trifluoroacetate salt to Cetrorelix acetate salt by desalting and exchanging with suitable salt by passing through resin and acid.

9. The process as claimed in claim 8, wherein Cetrorelix trifluoroacetate salt is desalted by passing over suitable basic resin selected from macroporous strongly basic anion exchange resin in chloride form with Sty-DVB matrix and Benzyl trimethyl amine as functional group, PolyAPTAC, or poly (acrylamido-N-propyltrimethylammonium chloride) and PolyMAPTAC, or poly[(3-(methacryloylamino)-propyl] trimethylammonium chloride) and suitable acid used is glacial acetic acid.

10. A Cetrorelix acetate having purity greater than 99% by HPLC and wherein one or more of the following
    a. less than 1.0% (w/w) of impurity A;
    b. less than 1.0% (w/w) of impurity B;
    c. less than 1.0% (w/w) of impurity C;
    d. less than 1.0% (w/w) of impurity D; and
    e. heavy metals less than 10 ppm.

\* \* \* \* \*